United States Patent
Joie et al.

(10) Patent No.: US 7,032,910 B2
(45) Date of Patent: Apr. 25, 2006

(54) ADAPTABLE BLOOD PROCESSING PLATFORMS

(75) Inventors: Michel Joie, Emage (BE); Tom Westberg, Gurnee, IL (US); Michael Niemotka, Mundelein, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/144,662

(22) Filed: May 13, 2002

(65) Prior Publication Data

US 2003/0209884 A1 Nov. 13, 2003

(51) Int. Cl.
*B62B 1/26* (2006.01)

(52) U.S. Cl. ............................ 280/47.131; 280/47.18
(58) Field of Classification Search ................ 280/38, 280/649, 43.1, 47.131, 47.18
See application file for complete search history.

(56) References Cited

U.S. PATENT DOCUMENTS

| | | | | | |
|---|---|---|---|---|---|
| 2,809,047 | A | * | 10/1957 | Strohmaier | 280/654 |
| 3,008,463 | A | * | 11/1961 | Frank | 126/9 R |
| 3,684,307 | A | * | 8/1972 | Bourgraf et al. | 280/654 |
| 4,053,104 | A | * | 10/1977 | Penhasi et al. | 494/14 |
| 4,565,382 | A | * | 1/1986 | Sherman | 280/47.18 |
| 4,570,912 | A | * | 2/1986 | Dodson et al. | 267/64.15 |
| 4,824,081 | A | * | 4/1989 | Pauliukonis | 267/64.12 |
| 4,921,225 | A | * | 5/1990 | Ludwig | 267/64.13 |
| 4,934,718 | A | * | 6/1990 | Voegele | 280/30 |
| 5,002,293 | A | * | 3/1991 | Gottselig | 280/47.35 |
| 5,927,745 | A | * | 7/1999 | Cunningham | 280/652 |
| 5,957,472 | A | * | 9/1999 | Borgatti | 280/30 |
| 6,196,560 | B1 | * | 3/2001 | Ohlsson | 280/30 |
| 6,284,142 | B1 | * | 9/2001 | Muller | 210/745 |
| 6,328,319 | B1 | * | 12/2001 | Stahler, Sr. | 280/47.18 |
| 6,345,829 | B1 | * | 2/2002 | Mueller | 280/47.18 |
| 6,471,236 | B1 | * | 10/2002 | Eskridge | 280/648 |
| 6,578,856 | B1 | * | 6/2003 | Kahle | 280/30 |

* cited by examiner

*Primary Examiner*—Christopher P. Ellis
*Assistant Examiner*—Christopher Bottorff
(74) *Attorney, Agent, or Firm*—James S. Pristelski; Bradford R. L. Price

(57) ABSTRACT

An adaptable blood processing platform comprises a blood processing device and a ground engaging frame including a shelf to which the blood processing device is secured. The frame supports the shelf for movement between a lowered position and a raised position. The shelf can be supported, e.g., for swinging cantilevered movement about an axis between the lowered and raised positions. The shelf can be supported, e.g., by a scissors linkage assembly coupled to the shelf for lowering and lifting the shelf between a lowered and raised positions. In the lowered position, the center of gravity of the blood processing device is located a first distance above ground, which is conducive for stable storage and/or transport of the platform. In the raised position, the center of gravity of the blood processing device is located a second distance above ground greater than the first distance, which is conducive for set-up and operation of the platform.

12 Claims, 10 Drawing Sheets

ADAPTABLE BLOOD PROCESSING PLATFORMS

FIELD OF THE INVENTION

This invention generally relates to systems and methods for processing and collecting blood, blood constituents, or other suspensions of cellular material. More particularly, this invention relates to the transport, set-up, and support of blood processing devices prior to, during, and/or after use.

BACKGROUND OF THE INVENTION

Today people routinely separate whole blood, usually by centrifugation, into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Blood processing equipment is typically of a size that does not permit easy transport or storage at a blood collection site, particularly when the site is remote from a dedicated collection facility. Furthermore, set-up of conventional blood processing equipment at the blood collection site for operation can sometimes be time consuming and tedious.

SUMMARY OF THE INVENTION

The invention provides adaptable blood processing platforms that lend themselves to easy storage, transport, set-up, and operation.

According to one aspect of the invention, an adaptable blood processing platform comprises a blood processing device and a ground engaging frame including a shelf to which the blood processing device is secured. The frame supports the shelf for movement between a lowered position and a raised position. The shelf can be supported, e.g., for swinging cantilevered movement about an axis between the lowered and raised positions, or by a scissors linkage assembly coupled to the shelf for lowering and lifting the shelf between the lowered and raised positions.

In the lowered position, the center of gravity of the blood processing device is located a first distance near the ground, which is conducive for stable storage and/or transport of the platform. In the raised position, the center of gravity of the blood processing device is located a second distance farther above ground than the first distance, which is conducive for stable set-up and use of the platform by an operator.

The frame desirably includes at least one ground engaging wheel for transporting the frame. The frame can include a handle for maneuvering the frame during transport on the at least one ground engaging wheel.

Another aspect of the invention provides a blood processing method that makes use of an adaptable blood processing platform as just described. The method transports the blood processing device on the frame while the shelf is in the lowered position. The method operates the blood processing device on the frame while the shelf is in the raised position.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
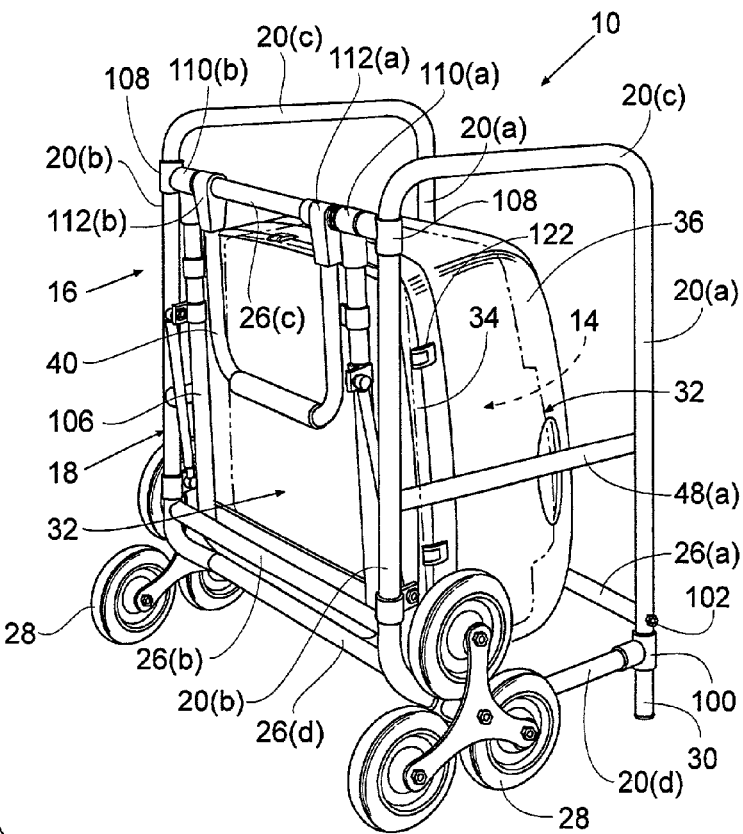
FIG. 1 is a perspective rear view of an adaptable blood processing platform, in which a blood processing device is supported by the platform in an enclosed, lowered position conducive for storage.

FIG. 1 shows a portable blood processing platform 10 that lends itself to easy storage, transport, set-up, and operation. The platform 10 can be used in association with various blood processing functions or systems. The platform 10 is particularly well suited for processing whole blood and other suspensions of biological cellular materials. Accordingly, the illustrated embodiment shows the platform 10 used for this purpose. However, the applicability of the platform for use in other blood processing environments should be appreciated, e.g., washing or salvaging blood cells during surgery, or therapeutic plasma exchange, or in any other procedure where blood is circulated in an extracorporeal path for treatment, such as hemodialysis, peritoneal dialysis, blood filtration, etc.

Figure 2:
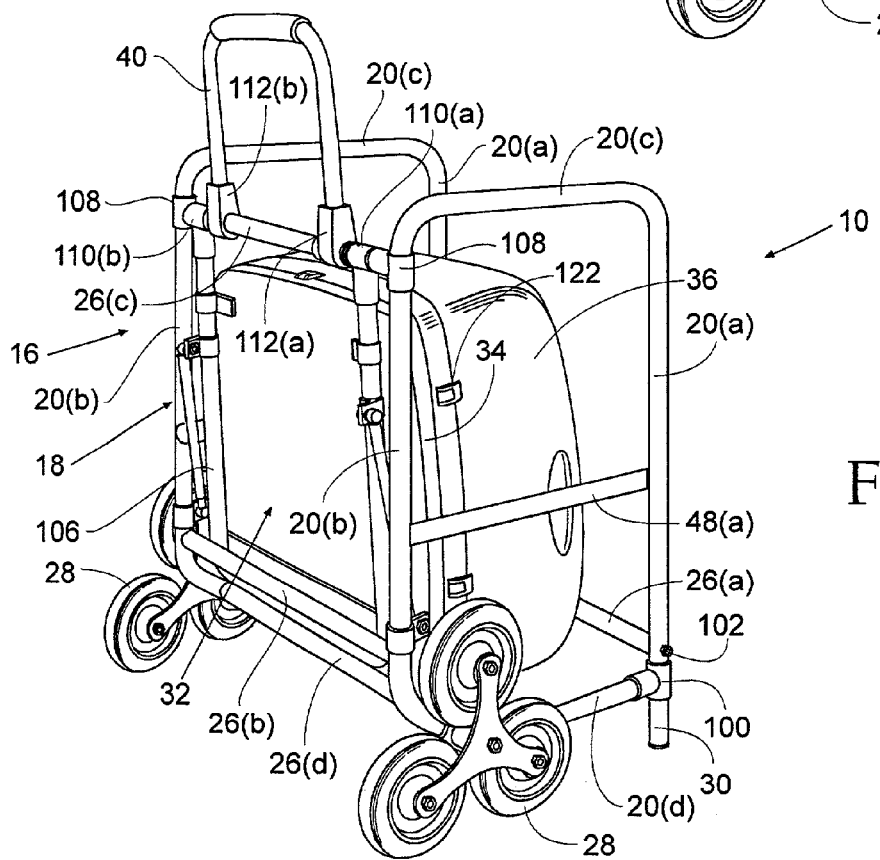
FIG. 2 is a perspective rear view of the adaptable blood processing platform shown in FIG. 1, in which the blood processing device is supported by the platform in the enclosed, lowered position and a transport handle on the platform has been extended for use.
Figure 3:
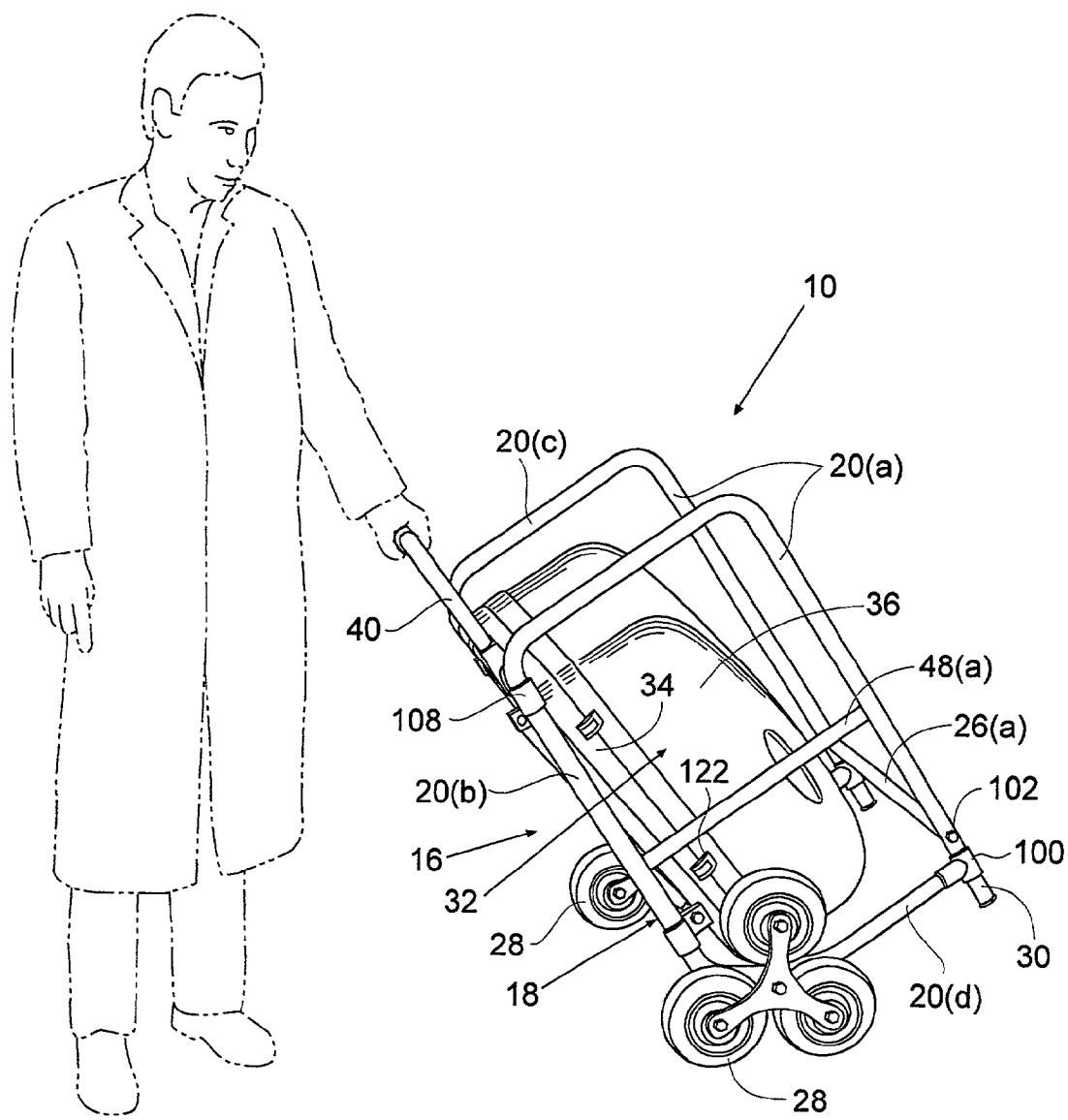
FIG. 3 is a perspective side view of the adaptable blood processing platform shown in FIG. 2 being transported by an operator.
Figure 4:
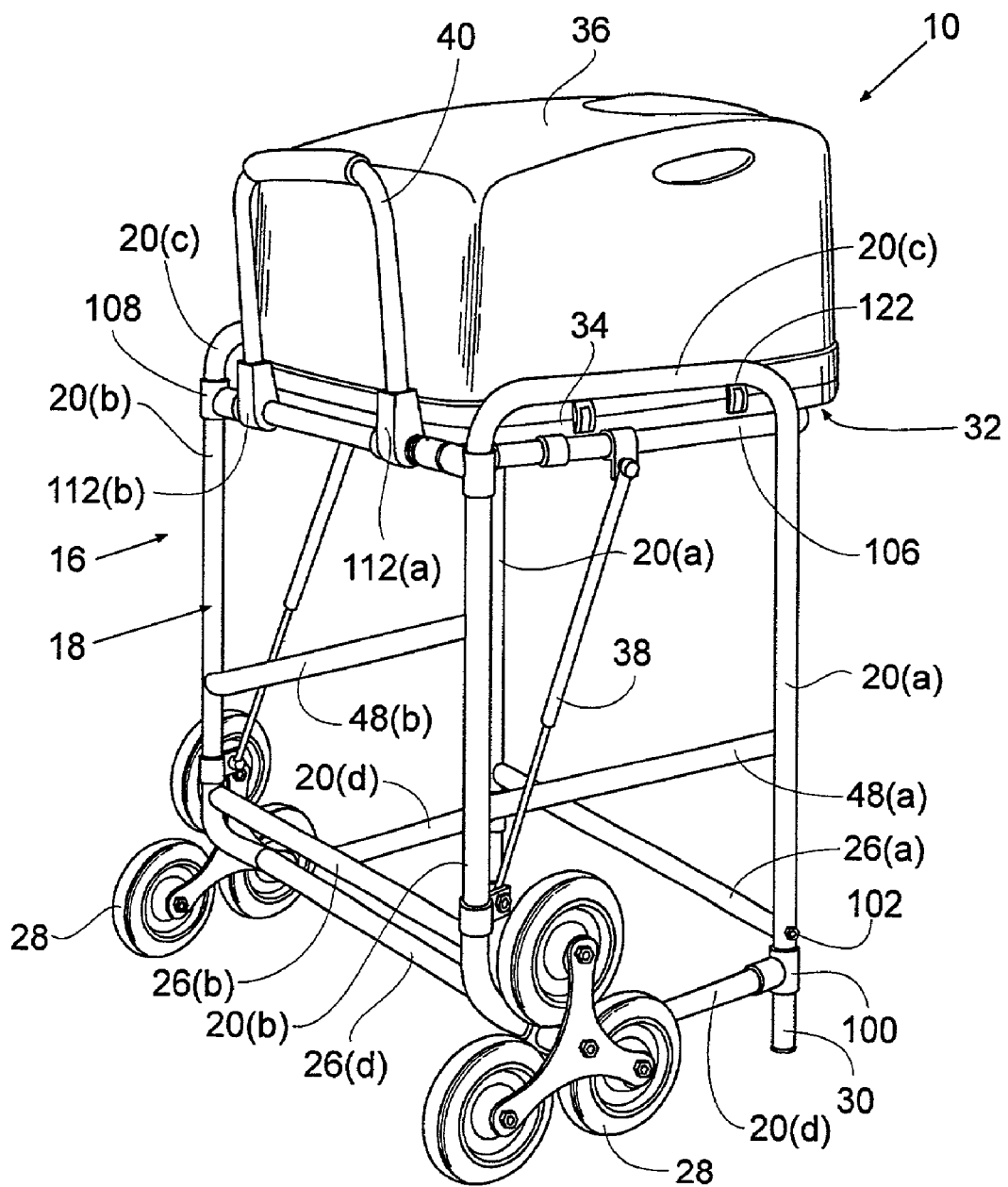
FIG. 4 is a perspective rear view of the adaptable blood processing platform shown in FIG. 1, in which the blood processing device is supported by the platform in an enclosed but now raised position ultimately conducive for set-up and operation.
Figure 5:
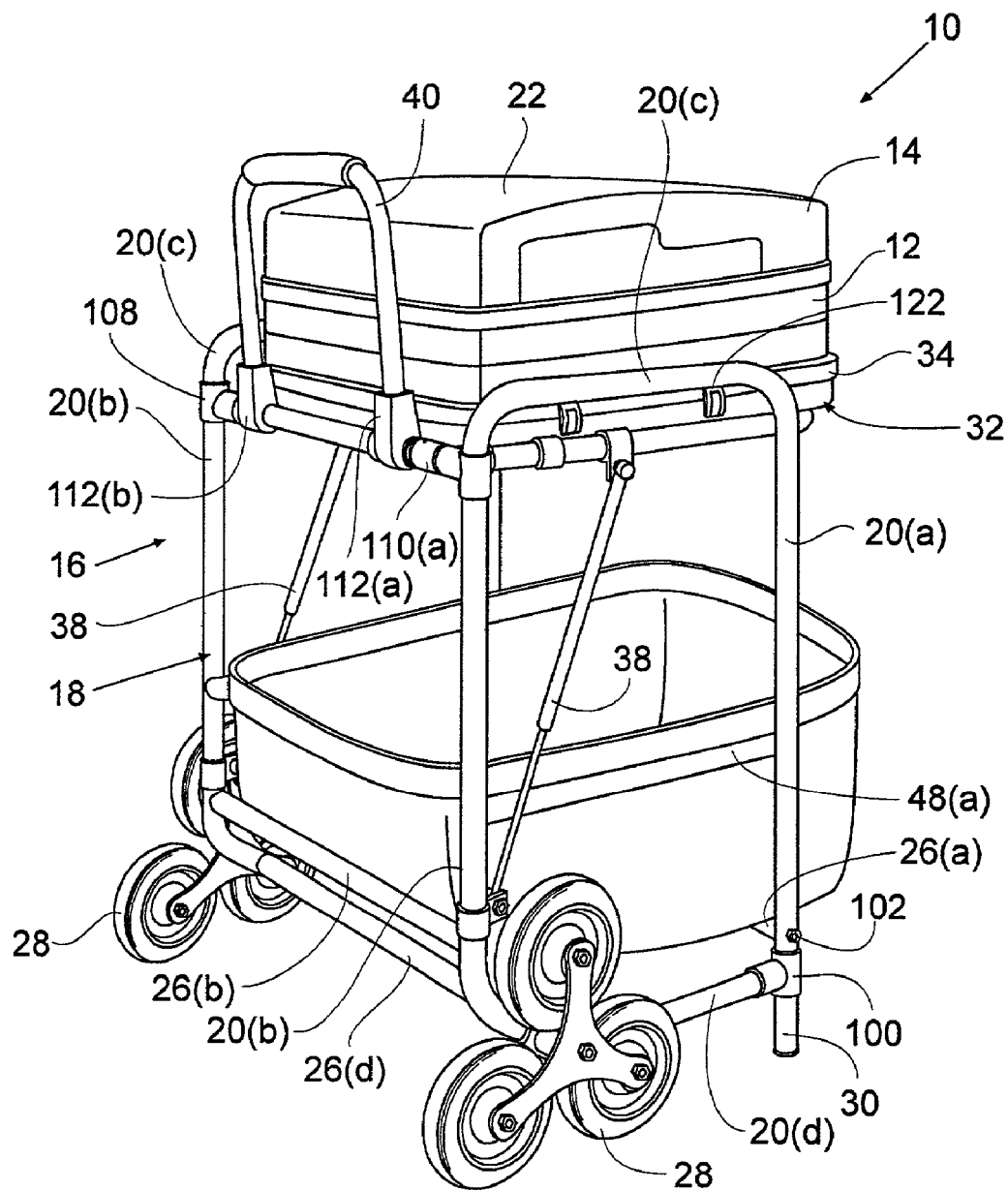
FIG. 5 is a perspective rear view of the adaptable blood processing platform shown in FIG. 4, in which the blood processing device is supported by the platform in the raised position, and a cover heretofore enclosing the blood processing device has been removed and stowed, exposing the device for set-up and operation.
Figure 6:
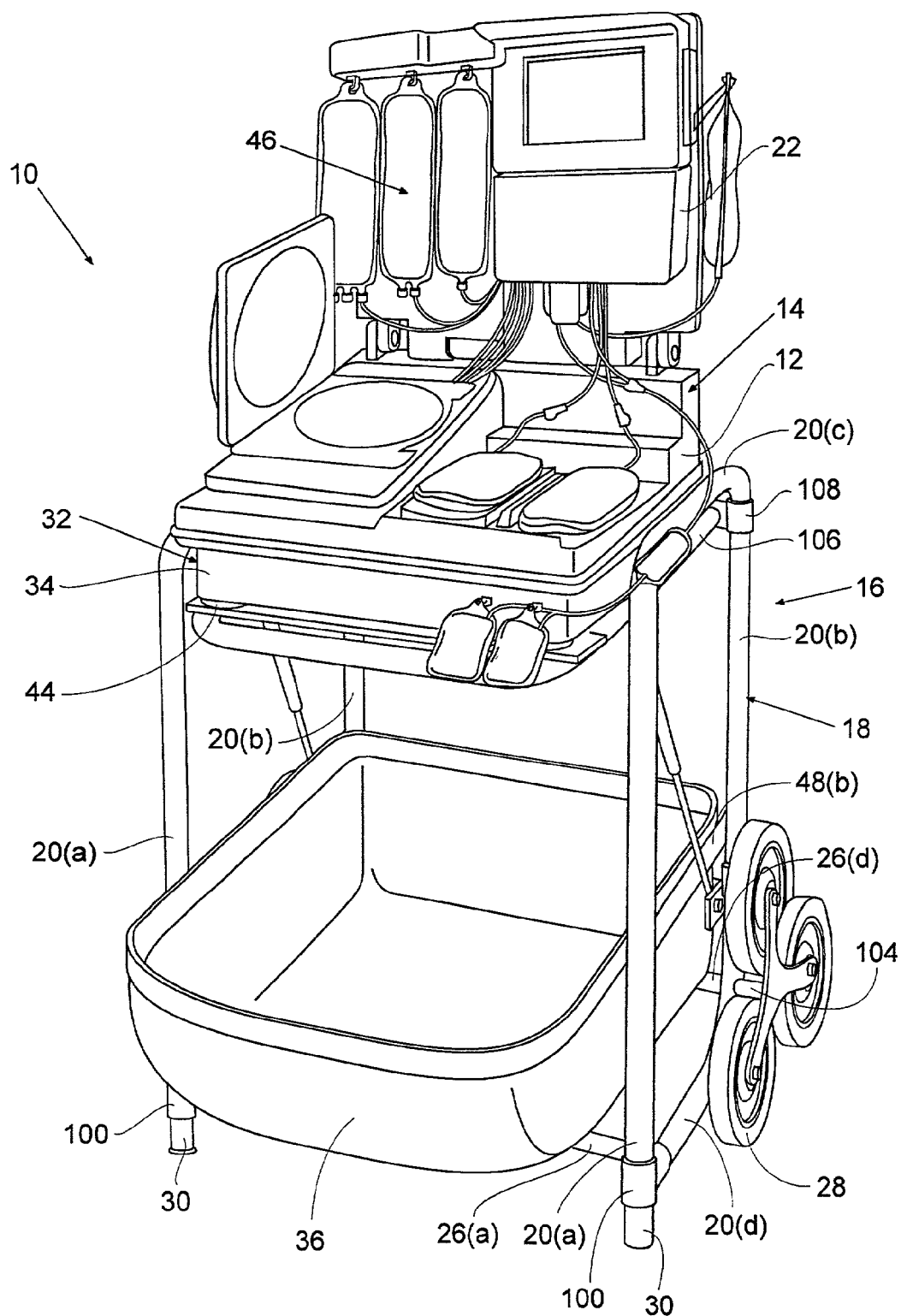
FIG. 6 is a perspective front view of the adaptable blood processing platform shown in FIG. 5, in which the blood processing device is supported by the platform in the raised, exposed position, and the device has been set-up and is ready for operation.

The platform 10 includes a cart 16 that carries a blood processing device 14 (shown in phantom lines in FIG. 1). As FIGS. 1 to 6 show, the cart 16 can be transformed into different functional configurations, to adapt the cart 16 to different modes of use. FIG. 1 shows the configuration of the cart 16 adapted to facilitate storage of the device 14 between periods of use. FIGS. 2 and 3 show the configuration of the cart 16 adapted to facilitate transport of the device 14 to an operational site. FIGS. 4 to 6 show the configuration of the cart 16 adapted to facilitate set-up and operation of the device 14.

The adaptable cart 16 can be constructed in various ways. In the embodiment shown in FIGS. 1 to 6, the cart 16 includes a unified frame 18 made, e.g., of a lightweight formed or extruded plastic material, or a lightweight formed or extruded metal material, or both.

The frame 18 comprises side frame members 20 formed from aluminum stock. In the illustrated embodiment, the aluminum stock is formed into fore and aft risers 20(a) and 20(b) respectively, and top and bottom cross members, respectively 20(c) and 20(d), spanning the risers 20(a) and 20(b). In this arrangement, the bottom cross members 20(d) can be joined to the fore risers 20(a), e.g., by a tee 100 or other suitable means, which can include welding.

Portions of the fore risers 20(a) extend a distance below their junction with the bottom cross members 20(d), providing forward, ground engaging support legs 30. As will be described in greater detail later, the legs 30 help support the frame 18 in an upright position, as FIGS. 1 and 2 show.

To structurally link the side frame members 20 and provide a unified frame, the frame 18 further includes front and back, bottom transverse frame members 26(a) and 26(b), respectively, spanning between the fore and aft risers 20(a) and 20(b), as well as a top transverse frame member 26(c), which spans the aft risers 20(b).

In the illustrated embodiment, the transverse frame members 26(a) and 26(b) are formed from aluminum stock. The transverse frame members 26(a) and 26(b) can be secured to the fore and aft risers 20(a) and 20(b), e.g., by fasteners 102 or other suitable means, which can also include welding.

In the illustrated embodiment (best shown in FIG. 6), an axle 104 passes through an additional bottom transverse frame member 26(d), which is attached between the aft risers 20(b). The axle 104 supports left and right ground engaging wheel assemblies 28. Together, the wheel assemblies 28 and legs 30 support the frame 18 in an upright position, as FIGS. 1 and 2 show.

While two wheel assemblies are shown, it should be appreciated that a single, centrally balanced wheel assembly, or an array of three or more wheel assemblies could be used.

The wheel assemblies 28 can take various conventional forms. In the illustrated embodiment, each wheel assembly comprises a conventional pivoting tri-wheel arrangement is shown, to facilitate transport of the platform 10 up and down stairs.

The top transverse frame member 26(c) carries a cantilevered shelf frame 106 and an adjustable transport handle 40. Various types of construction are possible. In the illustrated embodiment, the top transverse frame member 26(c) is formed from aluminum stock and can be rigidly secured to the aft risers 20(b), e.g. by tees 108 or other suitable means, which can include welding.

The shelf frame 106 is coupled by sleeves 110(a) and 110(b) to the top transverse frame member 26(c). The sleeves 110(a) and 110(b) are sized to rotate freely on the top transverse frame member 26(c). This allows the shelf frame 106 to be lifted and lowered in cantilevered fashion on the top transfer frame member 26(c) in the space between the side frame members 20. By "cantilevered," it is meant that the shelf frame 106 is substantially supported only at one end, i.e., the end coupled to the top transverse frame member 26(c).

A shelf 32 is carried by the shelf frame 106. The shelf 32 includes a base 34, which is secured by screws or the like to the frame 106. The base 34 is made from, e.g., a lightweight molded plastic material. Carried by the shelf frame 106, the base 34 can be pivoted with the frame 106 between a lowered position (shown in FIGS. 1 to 3) and a raised, cantilevered position (shown in FIGS. 4 to 6).

A locking assembly 38 (see FIGS. 4 to 6) is desirably provided, to releasably lock the shelf frame 106 in a weight supporting condition when raised. In the illustrated embodiment, the locking assembly 38 takes the form of a pair of conventional locking air springs, which are coupled at one end to the aft risers 20(a) and at an opposite end to the shelf frame 106. The locking assembly 38 can, of course, take other suitable forms. In the illustrated embodiment, the locking air springs 38 are secured to apply an over-center force, so as to resist free swinging movement of the shelf frame 106 between its lowered and raised positions. The user thus must purposely lift or lower the shelf frame 106 past an over-center position to reach the raised and lowered positions.

In the illustrated embodiment, the handle 40 is made from aluminum stock formed into a conventional u-shaped configuration suited for convenient single-hand grasping by an operator. The handle 40 is secured by sleeves 112(a) and 112(b) to the top transverse frame member 26(c) inboard of the shelf sleeves 110(a) and 110(b). The sleeves 112(a) and 112(b) are sized to rotate freely on the top transverse frame member 26(c). This allows the handle 40 to be moved in pivoting fashion on the top transverse frame member 26(c), between a lowered, stowed position for storage (see FIG. 1) and a raised, transport position for maneuvering the cart 16 (see FIGS. 2 and 3).

Figure 7A:
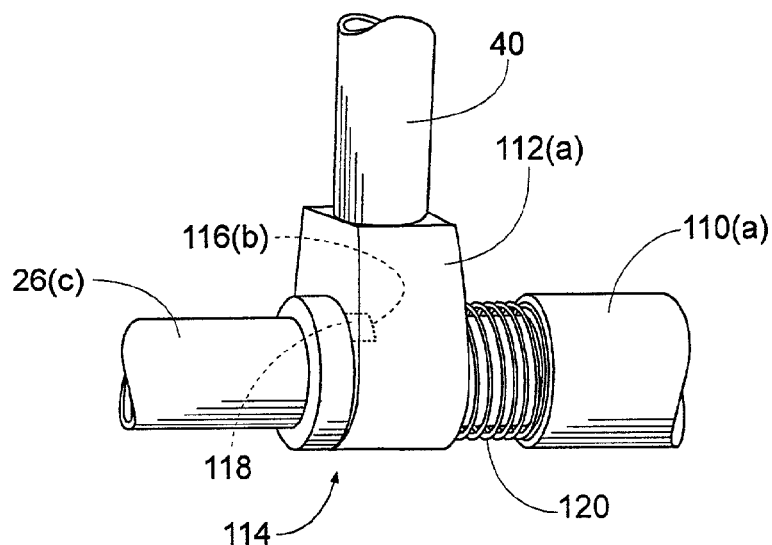
FIGS. 7A, 7B, and 7C are enlarged perspective views of a locking mechanism for the transport handle of the adaptable blood processing platform shown in FIG. 1, FIG. 7A showing the transport handle locked in its raised position for use (as also shown in FIGS. 2 and 3), FIG. 7B showing movement of the transport handle between its raised and stowed positions, and FIG. 7C showing the transport handle locked in its stowed position (as also shown in FIG. 1)
Figure 7B:
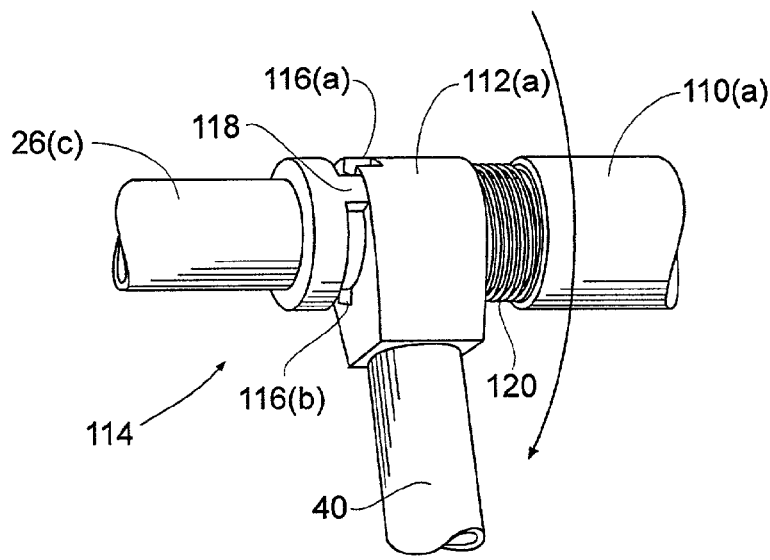
Figure 7C:
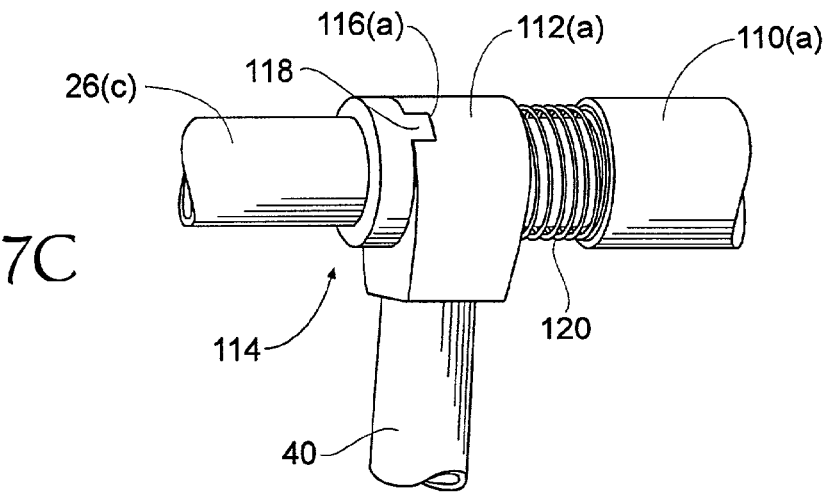

As best shown in FIGS. 7A, 7B, and 7C, a handle locking mechanism 114 is desirably provided to releasably lock the handle 40 in its lowered and extended positions. The locking mechanism 114 can be variously constructed. In the illustrated embodiment, the sleeve 112(a) includes circumferentially spaced keyways 116(a) and 116(b). During pivotal movement of the handle 40, the keyways 116(a) and 116(b) move into and out of registration with a key 118 secured to the top transverse frame member 26(c) next to the sleeve 112(a).

A spring 120 is carried by the top transverse frame member 26(c) in a space between the shelf frame sleeve 110(*a*) and the handle sleeve 112(*a*). The spring 120 normally biases the handle sleeve 112(*a*) toward the key 118 (as FIGS. 7A and 7C show). The spring force is selected to permit the handle 40 to be manually displaced by a user along the top transverse frame member 26(*c*) away from the key 118 (as FIG. 7B shows). When displaced, the handle 40 is free to pivot on the top transverse frame member 26(*c*) for movement between its stowed and transport positions.

When the handle 40 is displaced and moved by the user into its stowed position (FIG. 7C), the key-way 116(*a*) registers with the key 118. When the user relieves the displacing force, the spring 120 urges the sleeve 112(*a*) toward the key 118, and the key 118 engages the keyway 116(*a*). The handle 40 is thereby locked in its lowered position.

Likewise, when the handle 40 is displaced and moved by the user into its transport position (FIG. 7A), the keyway 116(*b*) registers with the key 118. When the user relieves the displacing force, the spring 120 urges the sleeve 112(*a*) toward the key 118, and the key 118 engages the keyway 112(*b*). The handle 40 is thereby locked in its extended position.

Various other configurations can be used to provide a movable handle 40. For example, the handle 40 can be telescopically carried in tracks secured to the underside of the shelf frame 106, allowing the handle 40 to be extended for use and collapsed for storage. Alternatively, the handle 40 can be secured in a permanent transport position.

When the handle 40 is extended for use (see FIG. 3), the cart 16 can be conveniently tipped rearward in a stable manner about the wheel assemblies 28 and transported, dolly-style, in front of or behind an upright and walking user. From this transport position, the cart 16 can also be tipped forward in a stable manner and returned to an upright position (shown in FIGS. 1 and 2). In this position, which is conducive for storing the platform 10, the base 34 is oriented in a lowered, generally non-horizontal condition with respect to the ground, which can include a range of non-horizontal positions approaching and including true vertical. The bottom legs 30 and wheel assemblies 28 engage the ground and keep the upright cart 16 in an attitude such that the base 34, when raised into its cantilevered position, is oriented in a stable non-vertical position for supporting the device 14 for use, which can include a range of non-vertical positions approaching and including true horizontal.

The blood processing device 14 is secured to the base 34 (see FIGS. 4 and 5), e.g., by suitable screw mounts 44 (see FIG. 6), which can include springs or resilient materials to isolate the device 14 from the cart 16. Carried by the base 34, the blood processing device 14 itself can be raised and lowered with the base 34, as FIGS. 1 to 6 show.

In the illustrated embodiment, the shelf 32 also desirably includes a removable cover 36 that fits over the base 34. Suitable latches 122 can be used to removably secure the cover 36 to the base 34. When fitted to the base 34, the cover 36 encloses the blood processing device 14 during storage and transport (see FIGS. 1 to 3). Upon removal, preferably after the base 34 is raised (see FIGS. 4 and 5), the cover 36 exposes the blood processing device 14 for use. After removal (see FIGS. 5 and 6), the cover 36 can be held by the frame 18 upon resters 48(*a*) and 48(*b*), which are secured by suitable means between the fore and aft risers 20(*a*) and 20(*b*) beneath the raised base 34. The resters 48 can be formed, e.g., from aluminum stock.

The blood processing device 14 is intended to be a durable item capable of long term use, by itself or in association with the cart 16. In the illustrated embodiment, the blood processing device 14 is itself contained within a housing or case 12, which presents a compact footprint. The case 12 is preferably made from a lightweight, yet durable, molded plastic material. The case 12 can include a hinged lid 22, which opens (as FIG. 6 shows) and closes (as FIG. 5 shows).

Carried by the cart 16, the blood processing device 14 can be stored and transported on the cart 16 within the enclosing shelf 32, when placed in a lowered position (FIGS. 1 to 3). The blood processing device 14 can then be pivoted upward on the cart 16 by swinging the enclosed shelf 32 into a raised position (FIG. 4). With the shelf 32 in the raised position, the shelf cover 36 can be removed and stowed (see FIG. 5) to expose the blood processing device 14. By opening the lid 22 of blood processing device 14, the blood processing device 14 is supported on the cart for set up and operation (FIG. 6).

The platform 10 makes stable and convenient storage, transport, set-up, and operation possible. With the enclosing shelf 32 in the lowered position (FIG. 1), the platform 10 provides enclosure and protection to the blood processing device 14 within the low profile and small footprint configuration of the cart 16. Due to its low profile and small footprint in this position, multiple platforms 10 can stored side by side in a small space.

Figure 8:
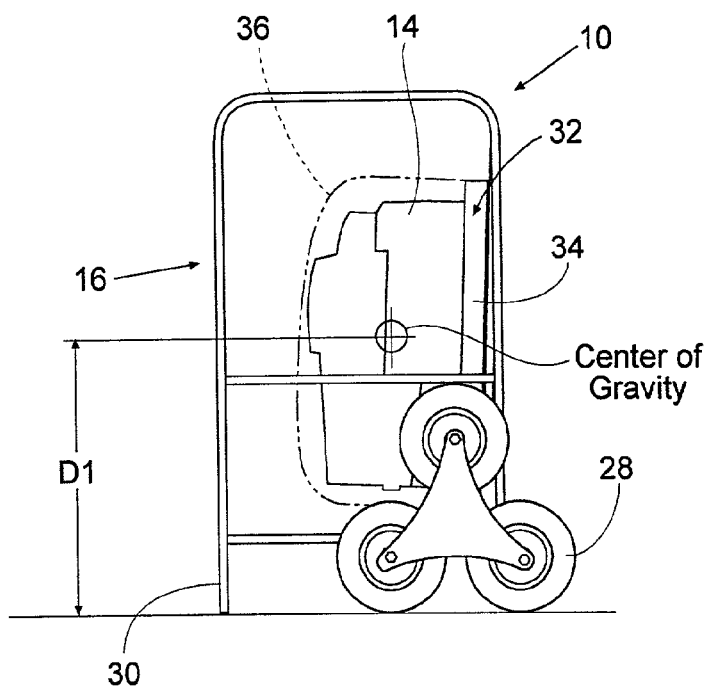
FIG. 8 is a diagrammatic side view of the adaptable blood processing platform shown in FIG. 1, showing the lowered location of the center of gravity of the blood processing device when the device is in the lowered position.

Confined within the enclosing shelf 32 in the lowered position (see FIG. 8), the center of gravity of the blood processing device 14 is held close to the ground at a first distance (D1 in FIG. 8). This allocation of weight close to the ground stabilizes the platform 10. Together with the low overall profile of the platform 10 in this condition, the allocation of weight close to the ground reduces the effort required to transport of the platform 10 in dolly-like fashion.

Figure 9:
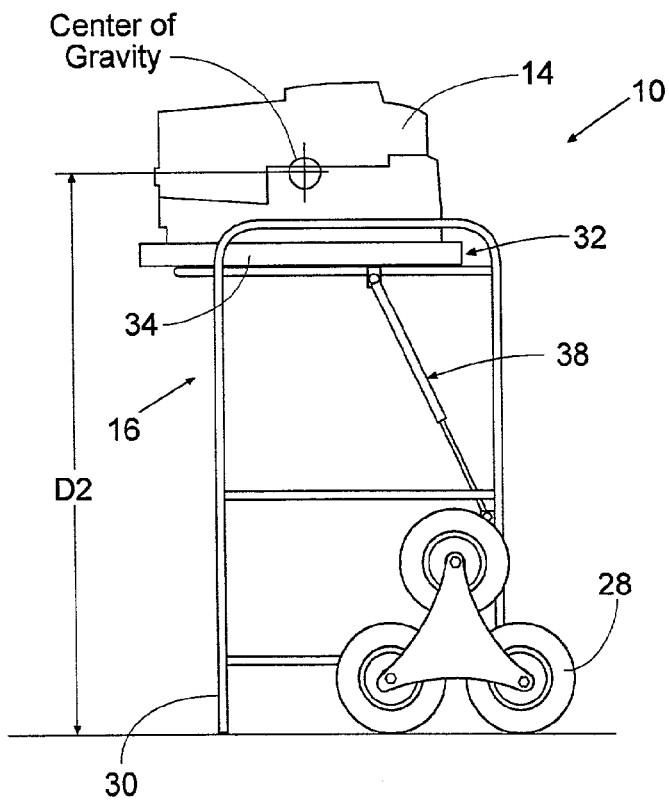
FIG. 9 is a diagrammatic side view of the adaptable blood processing platform shown in FIG. 4, showing the raised location of the center of gravity of the blood processing device when the device is in the raised position.

Confined within the enclosing shelf 32 (see FIG. 9), pivoting of the base 34 to the raised position likewise swings the blood processing device 14 into a stable, horizontal position for use. The lifting raises the center of gravity of the blood processing device 14 farther from the ground at a second distance (D2 in FIG. 9, which is greater than D1 shown in FIG. 8). The pivot axis of the shelf 32 (i.e., the top transverse frame member 26(*c*)) is desirably located at a predetermined distance above the ground (D3 in FIG. 9), such that the blood processing device 14, when in the raised position, is presented to the operator in a stable position and at an ergonomic height conducive for ease of set-up and operation, without undue bending, stooping, or reaching.

When in the stable, raised, ergonomically selected position (see FIG. 6), an operator can conveniently load a flow set 46 on the device 14. The flow set 46 includes tubing, bags, and other components used in association with the device to conduct a given blood processing procedure. The flow set 46 is intended to be a sterile, single use, disposable item. As FIG. 6 shows, before beginning a given blood processing and collection procedure, the operator loads various components of the flow set 46 in the case 36 and on the opened lid 22 in association with the device 14. Upon completing the procedure, the operator removes the flow set 46 from association with the device 14. The portion of the set 46 holding the collected blood component or components are retained for storage, transfusion, or further processing. The remainder of the set 46 is discarded.

Following use, the lid 22 of the device 14 can be closed, and the cover 36 returned to the base 34 to enclose the device 14. If desired, the platform 10 can retain the device 14 in the raised, enclosed position (FIG. 4) between periods of use, or the operator can return the platform 10 to the low profile storage and/or transport condition (FIG. 1) between periods of use.

Figure 10A:
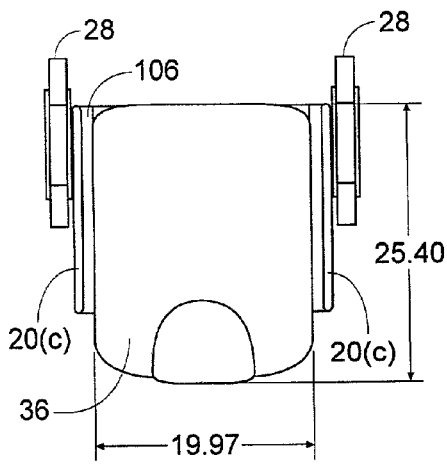
FIGS. 10A, 10B, and 10C are, respectively, top, front, and side plan views of the adaptable blood processing platform shown in its raised position (as in FIG. 4), showing representative dimensions.
Figure 10B:
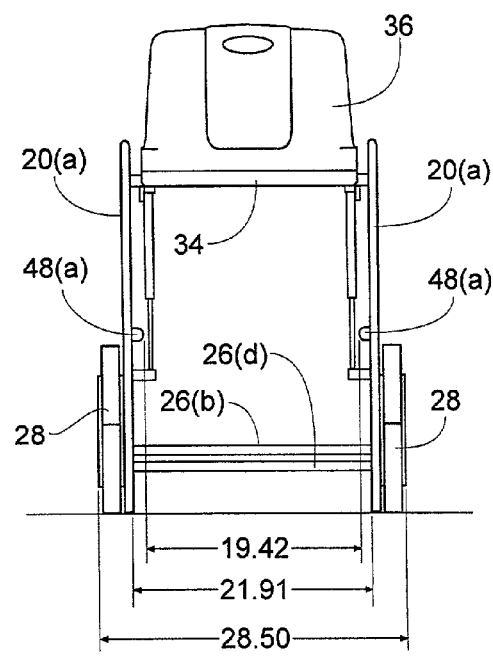
Figure 10C:
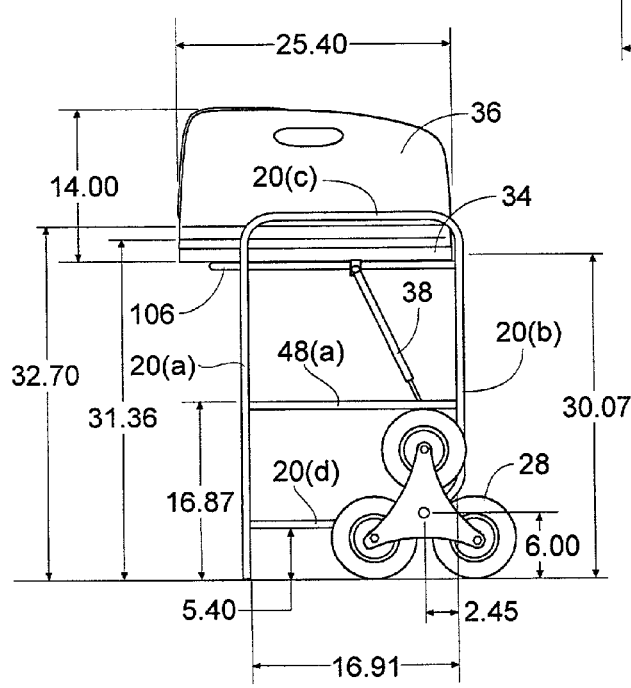

FIGS. 10A, 10B, and 10C show approximate dimensions (in inches) of a representative embodiment of a platform 10 having the technical features just described. A blood processing device 14 suited for use in association with the platform 10 is described in U.S. Pat. No. 6,261,065, which is incorporated herein by reference. As there described, the blood processing device 14 separates blood components from whole blood in an automated fashion by centrifugation.

Figure 11:
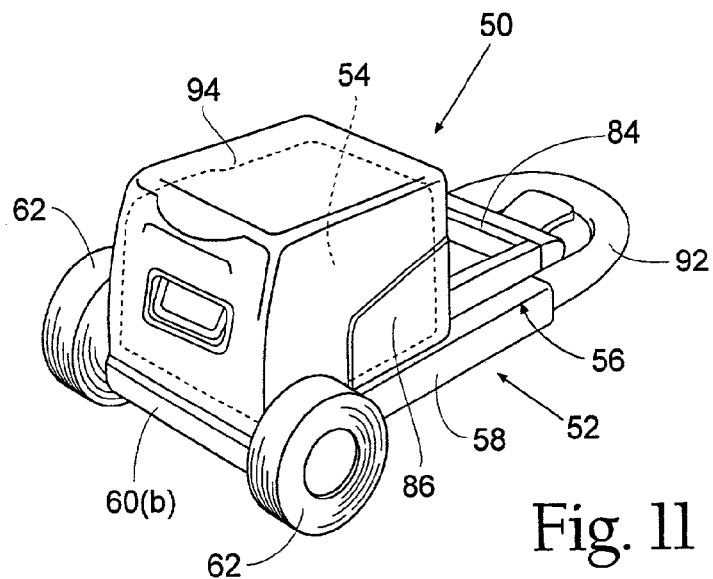
FIG. 11 is a perspective rear view of an alternative embodiment of an adaptable blood processing platform, in which a blood processing device is supported by the platform in an enclosed, lowered position conducive for storage.
Figure 12:
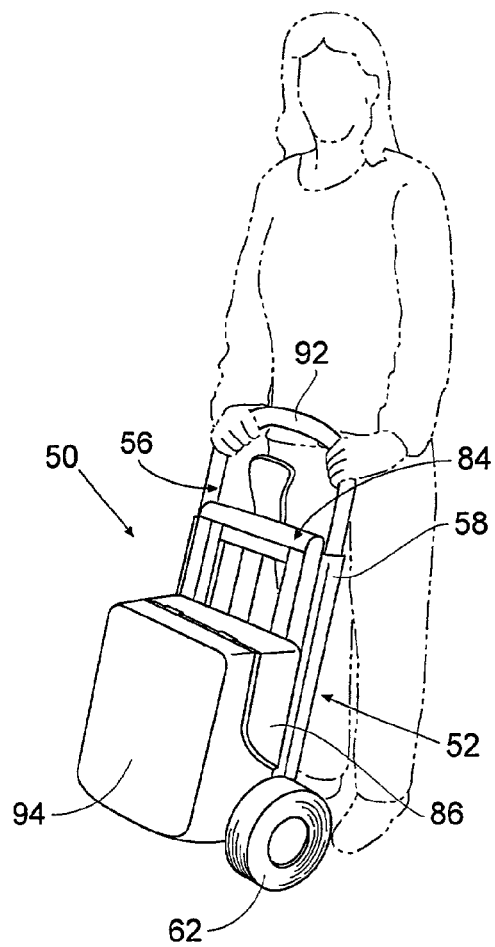
FIG. 12 is a perspective side view of the adaptable blood processing platform shown in FIG. 11 being transported by an operator.
Figure 13:
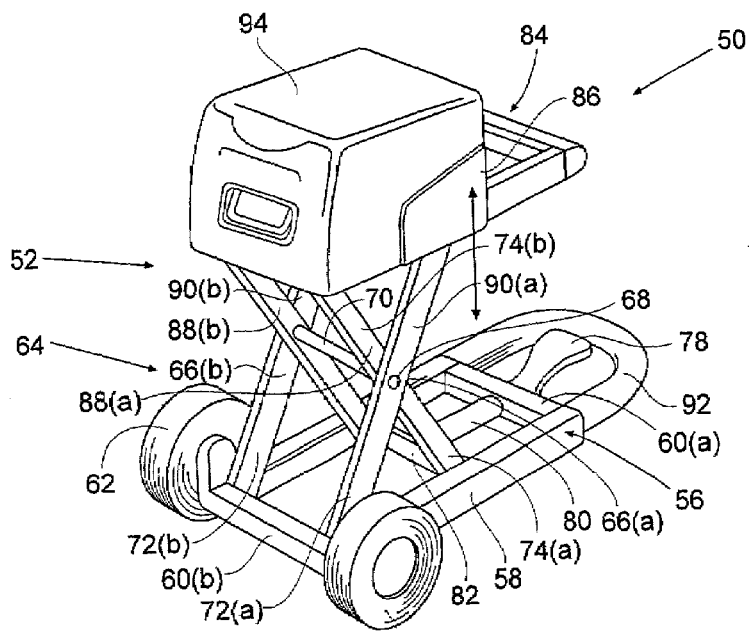
FIG. 13 is a perspective front view of the adaptable blood processing platform shown in FIG. 11, in which the blood processing device is supported by the platform in an enclosed but now raised position ultimately conducive for set-up and operation.
Figure 14:
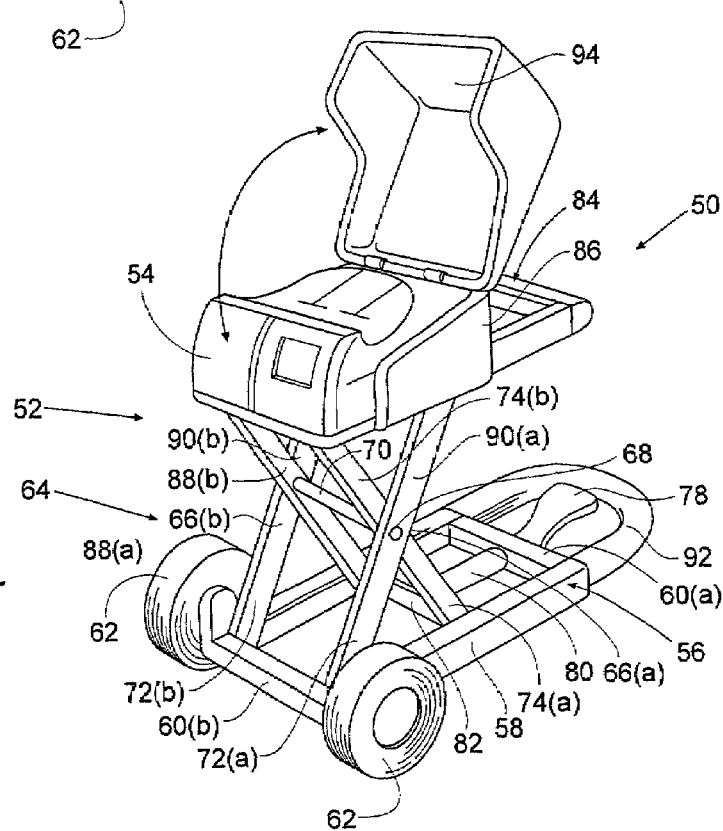
FIG. 14 is a perspective front view of the adaptable blood processing platform shown in FIG. 13, in which the blood processing device is supported by the platform in a raised and exposed position ready for set up and operation.

FIGS. 11 to 14 show another portable blood processing platform 50 that lends itself to easy storage, transport, set-up, and operation. Like the platform 10, the platform 50 can be used in association with various blood processing functions or systems. Like the platform 10, the platform 50 includes an adaptable cart 52 that carries a blood processing device 54 (shown in phantom lines in FIG. 11). As FIGS. 11 to 14 show, the cart 52 is adaptable by an operator, to transform the cart 52 into different configurations, each tailored to a particular function. FIG. 11 shows the configuration of the cart 52 adapted to facilitate storage of the device 54 between periods of use. FIG. 12 shows the configuration of the cart 52 adapted to facilitate transport of the device 54 to an operational site. FIGS. 13 and 14 show the configuration of the cart 52 adapted to facilitate set-up and operation of the device 54. In the embodiment shown in FIGS. 11 to 14, the cart 52 includes a frame 56 made, e.g., of a lightweight formed or extruded plastic material, or a lightweight formed or extruded metal material, or both. The frame 56 comprises a main frame member 58, which, in the illustrated embodiment, are made from aluminum stock bent into a generally U-shape. The frame 56 further includes top and bottom transverse frame members, 60(*a*) and 60(*b*), respectively (best exposed to view in shown in FIGS. 13 and 14), spanning in the main frame 58 in a spaced relationship. The transverse frame members 60(*a*) and 60(*b*) are coupled to the main frame 58 to impart rigidity and form a unified frame 56.

In the illustrated embodiment, the main frame 58 and transverse frame members 60(*a*) and 60(*b*) can be formed from aluminum stock.

Left and right wheel assemblies 62 are supported by the main frame 58 adjacent the bottom transverse frame member 60(*b*).

A scissors-linkage assembly 64 (see FIGS. 13 and 14) is coupled to the main frame 58. The scissors-linkage assembly 64 comprises left and right scissors links 66(*a*) and 66(*b*) coupled at their scissors axes 68 by a pivot bar 70. The bottom forward regions 72(*a*) and 72(*b*) of the scissors links 66(*a*) and 66(*b*) (i.e., adjacent the wheel assemblies 62) are pivotally joined by fixed bushings (not shown) to the main frame 58. The bottom rearward regions 74(*a*) and 74(*b*) of the scissors links 66(*a*) and 66(*b*) (away from the wheel assemblies 62) are slidably carried by facing parallel grooves 76 in the main frame 58. The bottom rearward regions 74(*a*) and 74(*b*) are thereby free to slide toward and away from the fixed bottom forward regions 72(*a*) and 72(*b*) in scissors fashion.

A foot actuated pump 78 on the main frame 58 is linked by a piston 80 by a cross bar 82 in tandem to the bottom rearward regions 74(*a*) and 74(*b*). Extension of the piston 80 in response to actuation of the pump 78 slides the bottom rearward regions 74(*a*) and 74(*b*) toward the fixed bottom forward regions 72(*a*) and 72(*b*). Relief of pump pressure allows retraction of the piston and allows the bottom rearward regions 74(*a*) and 74(*b*) to slide away from the fixed bottom forward regions 72(*a*) and 72(*b*).

The frame 56 further includes a shelf 84. The shelf 84 includes a base 86, which is made from, e.g., a lightweight molded plastic material. The base 86 is pivotally joined by bushings (not shown) to the top, forward and rearward regions 88(*a*)/88(*b*) and 90(*a*)/90(*b*) of the scissors links 66(*a*) and 66(*b*).

The scissors-linkage assembly 64 lifts the base 86 between a lowered position collapsed upon the frame 56 (shown in FIGS. 11 and 12) and a raised position above the frame 56 (shown in FIGS. 13 and 14). More particularly, extension of the piston 80 in response to actuation of the foot pump 78 slides the bottom rearward regions 74(*a*) and 74(*b*) toward the fixed bottom forward regions 72(*a*) and 72(*b*), thereby lifting the base 86. Relief of pump pressure allows retraction of the piston 80 and allows the bottom rearward regions 74(*a*) and 74(*b*) to slide away from the fixed bottom forward regions 72(*a*) and 72(*b*), thereby lowering the base 86. Pressure exerted by the pump 78 to extend the piston 80 will, until relieved, lock and support the base 86 when in its raised position.

The main frame 58 also forms a transport handle 92. Using the handle 92 (see FIG. 12), the cart 52 can be conveniently pivoted in a stable manner about the wheel assemblies 62 and transported, dolly-style, in front of or behind an upright operator. From this transport position, the cart 52 can also be tipped back in a stable manner into an essentially horizontal position on the ground (see FIG. 11). The main frame 58 engages the ground and keeps the cart 52 in an attitude such that the base 86, when raised, is generally parallel to the ground (see FIGS. 13 and 14).

As in the previously described platform 10, the blood processing device 54 carried by the platform 50 is secured to the base 86 (see FIG. 14), e.g., by screw mounts, which can include springs or resilient materials to isolate vibration of the device 54 from the cart 52. Carried by the base 86, the blood processing device 54 itself can be raised and lowered with the base 86, as FIGS. 11 to 14 show.

In the illustrated embodiment, the shelf 84 also includes a hinged cover 94 for the base 86. When closed (see FIGS. 11 to 13), the cover 94 encloses the blood processing device 54 during storage and transport. When opened, preferably after the base 86 is raised (see FIG. 14), the cover 94 exposes the blood processing device 54 for use.

Carried by the cart 52, the blood processing device 54 can be stored and transported on the cart 52 within the enclosing shelf 84, when placed in a lowered position (FIGS. 11 and 12). The blood processing device 54 can then be raised upward on the cart 52 by raising the enclosed shelf 84 into a raised position (FIG. 13). With the shelf 84 in the raised position, the shelf cover 94 can be opened (see FIG. 14) to expose the blood processing device 54. The blood processing device 54 is supported on the cart for set up and operation (FIG. 14). As before described, the blood processing device 54 can itself include a hinged cover.

The platform 50, like platform 10, makes stable and convenient storage, transport, set-up, and operation possible. With the enclosing shelf 84 in the lowered position (FIG. 11), the platform 10 provides enclosure and protection to the blood processing device 54 within the low profile and small footprint configuration of the cart 52. Due to its low profile and small footprint in this position, multiple platforms 10 can stored side by side in a small space.

As previously described in the context of the platform 10, confined by the platform 50 within the enclosing shelf 84 in the lowered position, the center of gravity of the blood processing device 54 is held close to the ground. This allocation of weight close to the ground stabilizes the platform 50, just as the platform 10 was stabilized for the same reason. Together with the low overall profile of the platform 50 in this condition, the allocation of weight close to the ground reduces the effort required to transport of the platform 10 in dolly-like fashion (see FIG. 12).

As previously described in the context of the platform 10, confined by the platform 50 within the enclosing shelf 84 (see FIG. 13), lifting the base 86 to the raised position likewise lifts the blood processing device 54 into a stable, horizontal position for use. The lifting raises the center of gravity of the blood processing device 54 farther from the ground at a second distance. As previously described in the context of the platform 10, the action of the scissors-linkage assembly 64 is selected to present the blood processing device 54, when in the raised position, to the operator at an ergonomic orientation conducive for ease of set-up and operation, without undue bending, stooping, or reaching.

Features of the invention are set forth in the following claims.

We claim:

1. A blood processing platform comprising:
a blood processing device having a center of gravity and a predetermined height, and
a ground engaging frame including a shelf to which the blood processing device is secured in all shelf positions, the frame supporting the shelf for movement about an axis between a lowered position suitable for transporting the blood processing device on the shelf, in which the center of gravity of the blood processing device is located a first distance above ground, and a raised, cantilevered position, suitable for operating the blood processing device on the shelf in which the center of gravity of the blood processing device is located a second distance above ground greater than the first distance;
said frame comprising a first and a second set of fore and aft risers, the distance between the fore riser of said first set and the aft riser of said first set at least equal to the height of said blood processing device;
said fore and aft risers substantially vertically disposed when the shelf is in the raised and lowered positions;
said frame further comprising a locking assembly that telescopes between a retracted condition and an extended condition, said locking assembly disposed between the frame and the shelf for supporting said shelf in the raised, cantilevered position when the locking assembly is in the extended condition and for permitting said shelf moved to said lowered position when said locking assembly is in the retracted condition.

2. A blood processing platform according to claim 1 wherein, in the lowered position, the shelf is supported in a generally non-horizontal orientation with respect to the ground, and
wherein, in the raised, cantilevered position, the shelf is supported in a generally non-vertical orientation with respect to the ground.

3. A blood processing platform according to claim 1 wherein the frame includes at least one ground engaging wheel for transporting the frame.

4. A blood processing platform according to claim 3 wherein the frame includes at least one ground engaging leg spaced from the ground engaging wheel, the leg and wheel together supporting the frame in an upright position during movement of the shelf between its lowered position and its raised, cantilevered position.

5. A blood processing platform according to claim 4 wherein the frame includes a handle for maneuvering the frame during transport on the at least one ground engaging wheel.

6. A blood processing platform according to claim 1 wherein the shelf includes a removable cover for enclosing the blood processing device.

7. A blood processing platform according to claim 1 wherein the frame includes a mechanism for releasably locking the shelf when in the raised position.

8. A blood processing method comprising the steps of:
mounting a blood processing device on a shelf such that the blood processing device is carried by a wheeled cart, the cart supporting the shelf for movement about an axis between a lowered position suitable for transporting the blood processing device on the shelf, in which the center of gravity of the blood processing device is located a first distance above ground, and a raised, cantilevered position, suitable for operating the blood processing device on the shelf in which the center of gravity of the blood processing device is located a second distance above ground greater than the first distance, with the blood processing device secured to the shelf in all shelf positions, said cart including a frame comprising a first and a second set of fore and aft risers, the distance between said first fore riser and said second fore riser at least equal to a width of said blood processing device, said fore and aft risers substantially vertically disposed when the shelf is in the raised and lowered positions, said frame further comprising a locking assembly that telescopes between a retracted condition and an extended condition, said locking assembly disposed between the frame and the shelf,
supporting said shelf in the raised, cantilevered position with the locking assembly when said locking assembly is in the extended condition,
permitting said shelf moved to the lowered position when said locking assembly is in the retracted condition,
transporting the blood processing device on the cart while the shelf is in the lowered position, and
operating the blood processing device on the cart while the shelf is in the raised, cantilevered position.

9. A blood processing method according to claim 8 wherein in the lowered position, the shelf is supported in a generally non-horizontal orientation with respect to the ground, and
wherein in the raised, cantilevered position, the shelf is supported in a generally non-vertical orientation with respect to the ground.

10. A blood processing method according to claim 8 further including the step of enclosing the blood processing device with a cover on the shelf.

11. A blood processing platform comprising:
a blood processing device having a center of gravity and a predetermined width, and a ground engaging frame including a shelf to which the blood processing device is secured in all shelf positions, the frame supporting the shelf for movement about an axis between a lowered position suitable for transporting the blood processing device on the shelf, in which the center of gravity of the blood processing device is located a first distance above ground, and a raised, cantilevered position, suitable for operating the blood processing device on the shelf in which the center of gravity of the blood processing device is located a second distance above ground greater than the first distance;
said frame comprising a first and a second set of fore and aft risers, the distance between said first fore riser and said second fore riser at least equal to the width of said blood processing device;
said fore and aft risers substantially vertically disposed when the shelf is in the raised or lowered positions;
said frame further comprising a locking assembly that telescopes between a retracted condition and an extended condition, said locking assembly disposed between the frame and the shelf for supporting said shelf in the raised, cantilevered position when the locking assembly is in the extended condition and for permitting said shelf moved to the lowered position when the locking assembly is in the retracted condition.

12. A blood processing platform comprising:

a blood processing device having a center of gravity and a predetermined width, and a ground engaging frame including a shelf to which the blood processing device is secured in all shelf positions, the frame supporting the shelf for movement about an axis between a lowered position for transporting the blood processing device on the shelf, in which the center of gravity of the blood processing device is located a first distance above ground, and a raised, cantilevered position, suitable for operating the blood processing device on the shelf in which the center of gravity of the blood processing device is located a second distance above ground greater than the first distance;

said frame comprising a first and a second set of fore and aft risers;

said fore and aft risers substantially vertically disposed when the shelf is in the raised or lowered positions;

a locking assembly that telescopes between a retracted condition and an extended condition, said locking assembly disposed between said frame and said shelf for applying over center force to said shelf when said shelf is in said lowered position and when said locking assembly is in the retracted condition to resist free swing movement of said shelf, and said shelf supported by the locking assembly in a weight supporting condition when the shelf is in said raised position and when said locking assembly is in the extended condition.

* * * * *